US012743833B2

(12) United States Patent
Chen et al.

(10) Patent No.: US 12,743,833 B2
(45) Date of Patent: Sep. 22, 2026

(54) SYSTEM AND METHOD FOR CONTROLLING ZERO-COUNT ERRORS IN COMPUTED TOMOGRAPHY

(71) Applicant: Wisconsin Alumni Research Foundation, Madison, WI (US)

(72) Inventors: Guang-Hong Chen, Madison, WI (US); Ke Li, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 762 days.

(21) Appl. No.: 17/994,779

(22) Filed: Nov. 28, 2022

(65) Prior Publication Data

US 2024/0177375 A1 May 30, 2024

(51) Int. Cl.
*G06T 12/10* (2026.01)
*A61B 6/03* (2006.01)
*G06T 12/30* (2026.01)

(52) U.S. Cl.
CPC ................ *G06T 12/10* (2026.01); *A61B 6/03* (2013.01); *G06T 12/30* (2026.01); *G06T 2211/40* (2013.01)

(58) Field of Classification Search
CPC .. G06T 11/005; G06T 11/008; G06T 2211/40; G06T 11/006; A61B 6/03; A61B 6/032; A61B 6/5205
USPC .......................................................... 382/131
See application file for complete search history.

(56) References Cited

U.S. PATENT DOCUMENTS

2012/0177173 A1* 7/2012 Xu ........................ G06T 11/005 378/19
2018/0204356 A1* 7/2018 Xia ....................... A61B 6/582

OTHER PUBLICATIONS

Knoll, Glenn F. Radiation Detection and Measurement. 4th Ed., John Wiley & Sons, 2010, (Specifically Chapter 3: "Counting Statistics and Error Prediction") (Year: 2010).*
K. Stephens, "FDA Approves Siemens Healthineers' Naeotom Alpha CT Scanner", AXIS Imaging News, Overland Park Oct. 1, 2021.

* cited by examiner

*Primary Examiner* — Jennifer Mehmood
*Assistant Examiner* — Dustin Bilodeau
(74) *Attorney, Agent, or Firm* — Quarles & Brady LLP

(57) ABSTRACT

A system and method for creating computed tomography (CT) images that includes acquiring or accessing CT data of a subject, identifying zero counts in the CT data, and replacing the zero counts in the CT data with at least one non-zero number to create zero-count free CT data. The method also includes estimating a probability function of the zero-count free CT data, removing bias in the zero-count free CT data using the probability function, and reconstructing the zero-count free CT data after removal of the bias to create a corrected image of the subject with preserved conditional independence and spatial resolution.

13 Claims, 8 Drawing Sheets
(3 of 8 Drawing Sheet(s) Filed in Color)

Corrected

Zero Weighted

SYSTEM AND METHOD FOR CONTROLLING ZERO-COUNT ERRORS IN COMPUTED TOMOGRAPHY

CROSS-REFERENCE TO RELATED APPLICATIONS

N/A

STATEMENT REGARDING FEDERALLY SPONSORED RESEARCH

N/A

BACKGROUND

The present disclosure relates to systems and methods for medical image data preparation, acquisition, and/or reconstruction. More particularly, systems and method are provided for controlling errors caused by zero-counts in computed tomography (CT) data.

In traditional computed tomography systems, an x-ray source projects a beam that is collimated to lie within an X-Y plane of a Cartesian coordinate system, termed the "imaging plane." The x-ray beam passes through the object being imaged, such as a medical patient, and impinges upon an array of radiation detectors. The intensity of the radiation received by each detector element is dependent upon the attenuation of the x-ray beam by the object and each detector element produces a separate electrical signal that relates to the attenuation of the beam. The linear attenuation coefficient is the parameter that describes how the intensity of the x-rays changes when passing through an object. Often, the "mass attenuation coefficient" is utilized because it factors out the dependence of x-ray attenuations on the density of the material. The attenuation measurements from all the detectors are acquired to produce the transmission map of the object.

The source and detector array in a conventional CT system are rotated on a gantry within the imaging plane and around the object so that the projection angle at which the x-ray beam intersects the object constantly changes. A group of x-ray attenuation measurements from the detector array at a given angle is referred to as a "view" and a "scan" of the object. These views are collected to form a set of views made at different angular orientations during one or several revolutions of the x-ray source and detector. In a two dimensional (2D) scan, data is processed to construct an image that corresponds to a 2D slice taken through the object. The prevailing method for reconstructing an image from 2D data is referred to in the art as the filtered backprojection (FBP) technique. This process converts the attenuation measurements from a scan into integers called "CT numbers" or "Hounsfield units," which are used to control the brightness of a corresponding pixel on a display.

Over the past 15 years, much effort has been committed to lowering radiation dose for x-ray CT imaging due to the potential cancer risks associated with the use of ionizing radiation in CT. Many efforts have been made to develop and commercialize systems and methods that enable low-dose CT imaging. Primarily, this has yielded noise-reduction algorithms that seek to reduce the inevitable decreases in SNR as dose is decreased. However, CT hardware with improved radiation dose efficiency, primarily x-ray detectors such as photon counting detectors, have also been studied and developed to enable low dose CT imaging.

Photon counting detector CT (PCD-CT) has been featured as one of the most important advances in low dose CT imaging due to its powerful noise rejection functionality in addition to other advantages such as spectral CT imaging capability. Currently, PCD-CT has been developed by major CT manufacturers for preclinical and clinical evaluations. The realization of PCDs in clinical CT imaging systems has sparked interest in the potential for PCDs to enable a new paradigm for radiation dose reduction in the x-ray imaging domain. The physical principles governing PCD technology provide inherent advantages compared to the conventional solid-state detectors employed in clinical CT systems. In terms of radiation dose reduction, the improved radiation dose efficiency and capacity to reduce or eliminate electronic noise via energy discrimination are the prominent attributes that make PCDs alluring for low-dose medical imaging applications.

Despite the theoretical and exhibited benefits of PCDs, many practical challenges must be addressed appropriately to realize the full potential of PCD-CT imaging in the low-dose regime. One such challenge that has yet to be adequately addressed for PCDs is the issue of registering a raw count of zero for a given detector element. To recover the line integrals of the linear attenuation coefficients, correcting for counts of zero in the raw CT data is imperative to avoid division-by-zero, when the logarithmic normalization operation is taken. The probability of registering a count of zero for a given detector element is significantly higher for PCDs when compared with conventional detectors. This increased probability is partially the result of the general one-to-one correspondence between the digital output of the PCD with the number of absorbed x-ray photons. PCDs use smaller detector pixels, which result in lower counts. Furthermore, some PCD detectors use the combination of semiconductors and absorbers with high atomic numbers such as tungsten between two semiconductors to absorb the scattered photon to reduce cross-talk, which results in lower counts. These inherent properties yielding zero counts apply irrespective of the number of bins used in for the PCD. As a matter of fact, the more bins, the greater the chance for zero counts in a given bin. That is, the allocation of raw counts to multiple energy bins for spectral CT imaging applications is another important consideration exacerbated in the face of zero counts. Additionally, PCDs have increased spatial resolution, with detector elements on the size of 0.1-0.3 mm, compared to EIDs with elements on the order of 1 mm or greater. The concern regarding zero counts becomes further exacerbated when imaging a large patient, or in the presence of a metallic or other highly-attenuating structure in the patient anatomy. In contrast, a single photon can generate tens to hundreds of digital counts in the elements of conventional energy integrating detectors (EIDs). Thus, in traditional detectors, the zero count problem is present, but at a substantially lower level of prevalence.

Thus, it would be desirable to have systems and methods for managing or overcoming errors resulting from zero-counts in CT data.

SUMMARY

The present disclosure provides systems and methods that overcome the aforementioned drawbacks by replacing zero counts with numbers that aim to simultaneously reduce statistical biases in CT number and noise variance of the resulted CT projection data.

In accordance with one aspect of the disclosure, a method is provided for creating computed tomography (CT) images that includes acquiring or accessing CT data of a subject, identifying zero counts in the CT data, and replacing the zero counts in the CT data with at least one non-zero number to create zero-count free CT data. The method also includes estimating a probability function of the zero-count free CT data, removing bias in the zero-count free CT data using the probability function, and reconstructing the zero-count free CT data after removal of the bias to create a corrected image of the subject with preserved conditional independence and spatial resolution.

In accordance with another aspect of the disclosure, a medical imaging system is provided that includes an x-ray source configured to deliver x-rays to an object as the x-ray source is rotated about the object, a detector having a plurality of detector elements configured to receive the x-rays and generate computed tomography (CT) data therefrom, and a controller configured to control the x-ray source to deliver the x-rays and to receive the CT data from the detector. The system also includes a processor configured to receive CT data of a subject from the detector, identify zero counts in the CT data, and replace the zero counts in the CT data with at least one non-zero number to create zero-count free CT data. The processor is further configured to estimate a probability function of the zero-count free CT data, remove bias in the zero-count free CT data using the probability function, and reconstruct the zero-count free CT data after removal of the bias to create a corrected image of the subject with preserved conditional independence and spatial resolution.

In accordance with one other aspect of the disclosure, a method is provided for creating computed tomography (CT) images that includes acquiring or accessing CT data of a subject, identifying zero counts in the CT data, and replacing the zero counts in the CT data with at least one non-zero number to create zero-count free CT data. The method also includes reducing a pre-log bias in the zero-count free CT data introduced by replacing of the zero counts with the at least one non-zero number, generating a sinogram estimator, reducing a post-log bias in the zero-count free CT data using the sinogram estimator, and reconstructing the zero-count free CT data after reducing the pre-log bias and the post-log bias to create an image of the subject.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
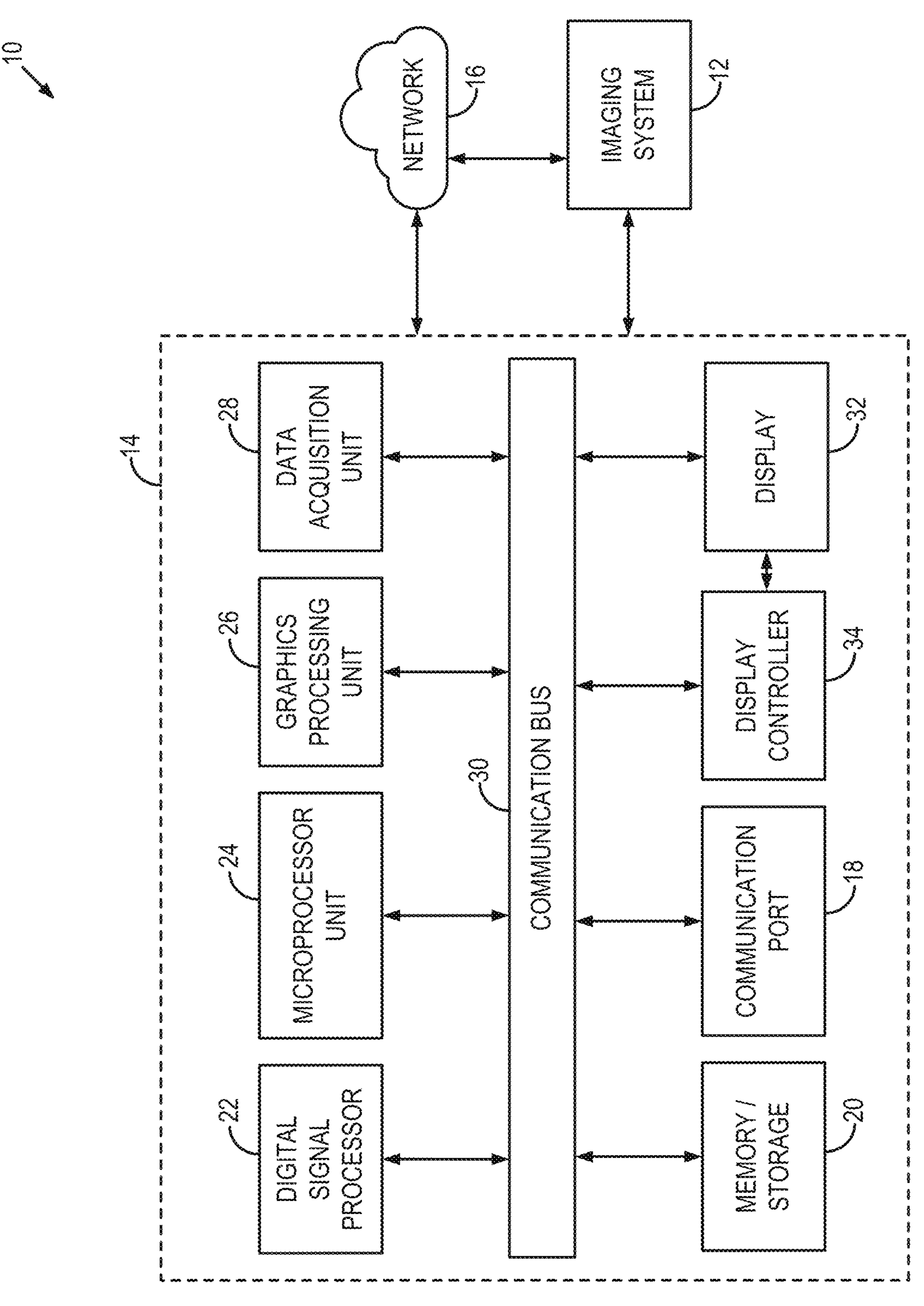
FIG. 1 is a schematic diagram of an example computer system that can be configured to implement the methods described herein.

Referring now to FIG. 1, a block diagram of an example system 10 is provided that can be configured to carry out techniques, methods, and processes accordance with the present disclosure. The system may include an imaging system 12 that is coupled to a computer system 14. The coupling of the imaging system 12 to the computer system 14 may be a direct or dedicated network connection, or may be through a broad network 16, such as an intranet or the Internet.

The computer system 14 may be a workstation integrated with or separate from the medical imaging systems 12 or a variety of other medical imaging systems, including, as non-limiting examples, computed tomography (CT) system, magnetic resonance imaging (MRI) systems, positron emission tomography (PET) systems, single photon emission computed tomography (SPECT) systems, and the like. Furthermore, the computer system 14 may be a workstation integrated within the medical imaging system 12 or may be a separate workstation or mobile device or computing system. To this end, the following description of particular hardware and configurations of the hardware of the example computer system 14 is for illustrative purposes. Some computer systems may have varied, combined, or different hardware configurations.

Medical imaging data acquired by the medical imaging system 12 or other imaging system can be provided to the computer system 14, such as over the network 16 or from a storage device. To this end, the computer system 14 may include a communications port or other input port 18 for communication with the network 16 and system coupled thereto. Also, the computer system 14 may include memory and storage capacity 20 to store and access data or images.

In some configuration, computer system 14 may include one or more processing systems or subsystems. That is, the computer system 14 may include one or more physical or virtual processors. As an example, the computer system 14 may include one or more of a digital signal processor (DSP) 22, a microprocessor unit (MPU) 24, and a graphics processing unit (GPU) 26. If the computer system 14 is integrated into the medical imaging system, a data acquisition unit 28 may be connected directly to the above-described processor(s) 22, 24, 26 over a communications bus 30, instead of communicating acquired data or images via the network 16. As an example, the communication bus 30 can be a group of wires, or a hardwire used for switching data between the peripherals or between any component, such as the communication buses described above.

The computer system 14 may also include or be connected to a display 32. To this end, the computer system 14 may include a display controller 34. The display 32 may be a monitor connected to the computer system 14 or may be integrated with the computer system 14, such as in portable computers or mobile devices.

Figure 2A:
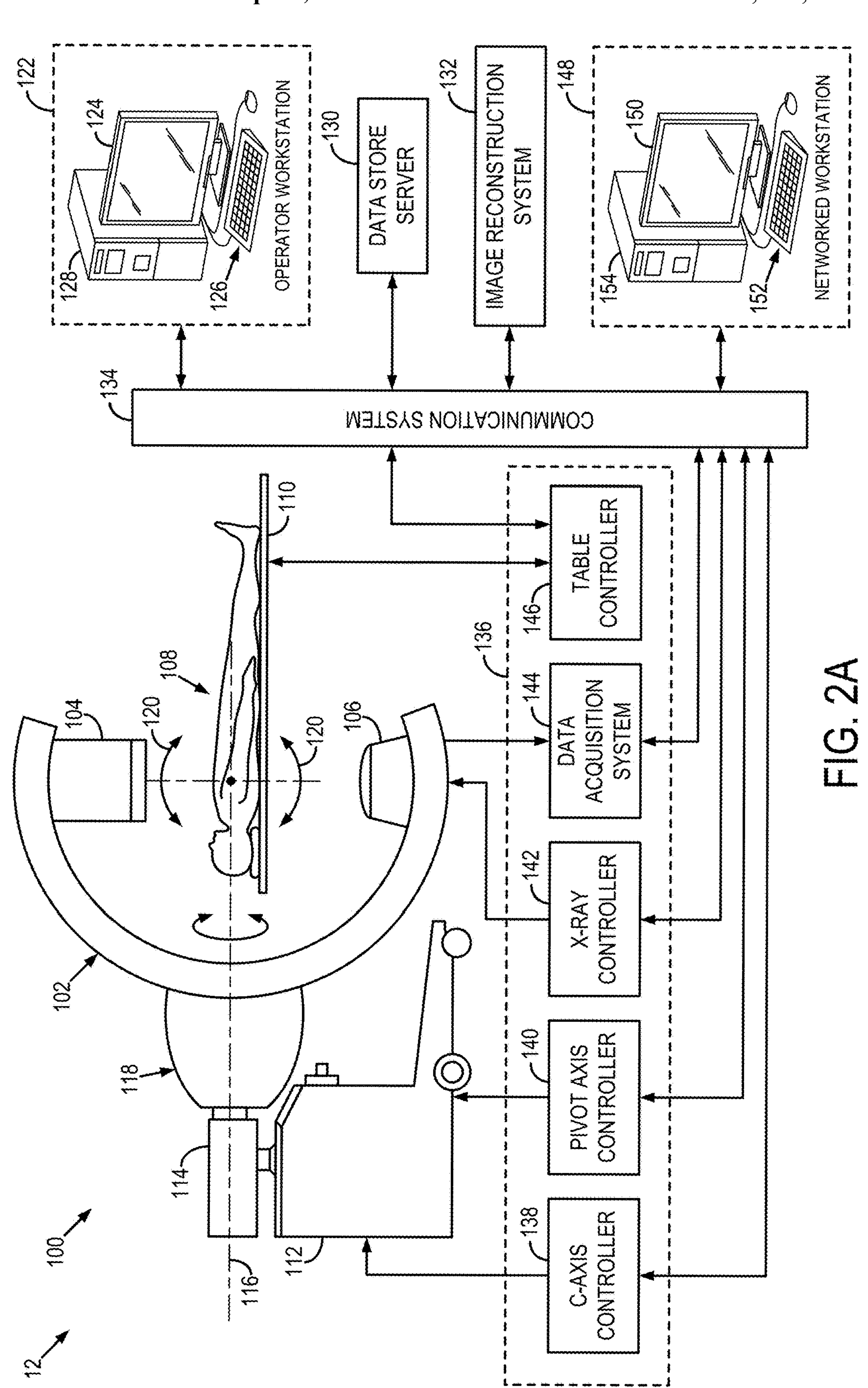
FIG. 2A is a schematic diagram of a C-arm x-ray computed tomography (CT) imaging system configured in accordance with the present disclosure.
Figures 2B, 2C:
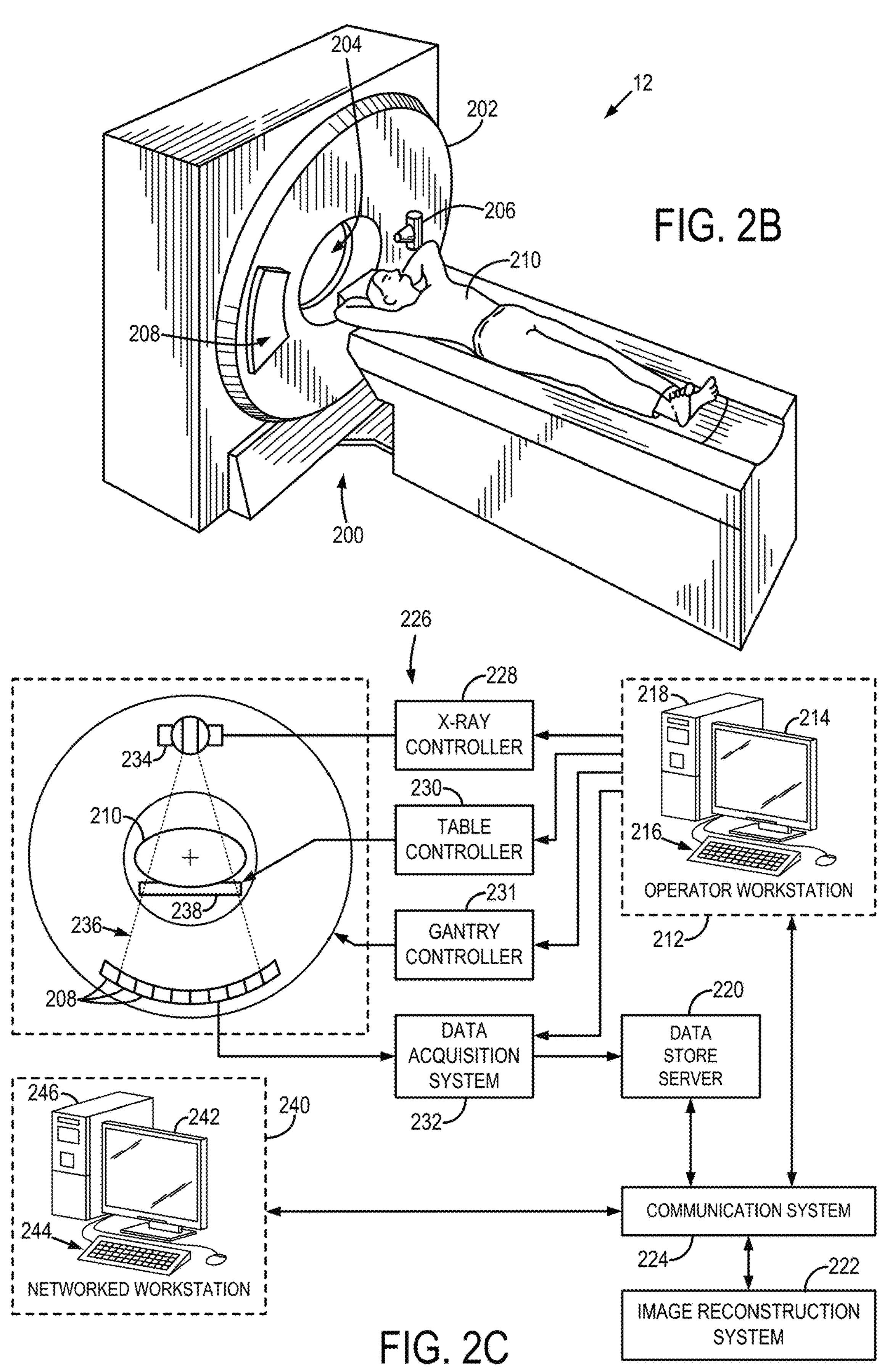
FIG. 2B is a perspective view of an example of an x-ray computed tomography (CT) system.
FIG. 2C is a block diagram of CT system, such as illustrated in FIG. 2B.

Referring to FIG. 2A, one, non-limiting example of the imaging system 12 of FIG. 1 is provided. Specifically, in this example, a so-called "C-arm" x-ray imaging system 100 is illustrated for use in accordance with some aspects of the present disclosure. Such an imaging system is generally designed for use in connection with interventional procedures. Such systems stand in contrast to, for example, traditional computed tomography (CT) systems 200, such as illustrated in FIG. 2B, which may also serve as an example of the imaging system 12 of FIG. 1.

Referring again to FIG. 2A, the C-arm x-ray imaging system 100 includes a gantry 102 having a C-arm to which an x-ray source assembly 104 is coupled on one end and an x-ray detector array assembly 106 is coupled at its other end. The gantry 102 enables the x-ray source assembly 104 and detector array assembly 106 to be oriented in different positions and angles around a subject 108, such as a medical patient or an object undergoing examination, which is positioned on a table 110. When the subject 108 is a medical patient, this configuration enables a physician access to the subject 108.

The x-ray source assembly 104 includes at least one x-ray source that projects an x-ray beam, which may be a fan-beam or cone-beam of x-rays, towards the x-ray detector array assembly 106 on the opposite side of the gantry 102. The x-ray detector array assembly 106 includes at least one x-ray detector, which may include a number of x-ray detector elements. Examples of x-ray detectors that may be included in the x-ray detector array assembly 106 include flat panel detectors, such as so-called "small flat panel" detectors. Such a detector panel allows the coverage of a field-of-view of approximately twelve centimeters.

Together, the x-ray detector elements in the one or more x-ray detectors housed in the x-ray detector array assembly 106 sense the projected x-rays that pass through a subject 108. Each x-ray detector element produces an electrical signal that may represent the intensity of an impinging x-ray beam and, thus, the attenuation of the x-ray beam as it passes through the subject 108. In some configurations, each x-ray detector element is capable of counting the number of x-ray photons that impinge upon the detector. During a scan to acquire x-ray projection data, the gantry 102 and the components mounted thereon rotate about an isocenter of the C-arm x-ray imaging system 100.

The gantry 102 includes a support base 112. A support arm 114 is rotatably fastened to the support base 112 for rotation about a horizontal pivot axis 116. The pivot axis 116 is aligned with the centerline of the table 110 and the support arm 114 extends radially outward from the pivot axis 116 to support a C-arm drive assembly 118 on its outer end. The C-arm gantry 102 is slidably fastened to the drive assembly 118 and is coupled to a drive motor (not shown) that slides the C-arm gantry 102 to revolve it about a C-axis, as indicated by arrows 120. The pivot axis 116 and C-axis are orthogonal and intersect each other at the isocenter of the C-arm x-ray imaging system 100, which is indicated by the black circle and is located above the table 110.

The x-ray source assembly 104 and x-ray detector array assembly 106 extend radially inward to the pivot axis 116 such that the center ray of this x-ray beam passes through the system isocenter. The center ray of the x-ray beam can thus be rotated about the system isocenter around either the pivot axis 116, the C-axis, or both during the acquisition of x-ray attenuation data from a subject 108 placed on the table 110. During a scan, the x-ray source and detector array are rotated about the system isocenter to acquire x-ray attenuation projection data from different angles. By way of example, the detector array is able to acquire thirty projections, or views, per second.

The C-arm x-ray imaging system 100 also includes an operator workstation 122, which typically includes a display 124; one or more input devices 126, such as a keyboard and mouse; and a computer processor 128. The computer processor 128 may include a commercially available programmable machine running a commercially available operating system. The operator workstation 122 provides the operator interface that enables scanning control parameters to be entered into the C-arm x-ray imaging system 100. In general, the operator workstation 122 is in communication with a data store server 130 and an image reconstruction system 132. By way of example, the operator workstation 122, data store server 130, and image reconstruction system 132 may be connected via a communication system 134, which may include any suitable network connection, whether wired, wireless, or a combination of both. As an example, the communication system 134 may include both proprietary or dedicated networks, as well as open networks, such as the Internet.

The operator workstation 122 is also in communication with a control system 136 that controls operation of the C-arm x-ray imaging system 100. The control system 136 generally includes a C-axis controller 138, a pivot axis controller 140, an x-ray controller 142, a data acquisition system (DAS) 144, and a table controller 146. The x-ray controller 142 provides power and timing signals to the x-ray source assembly 104, and the table controller 146 is operable to move the table 110 to different positions and orientations within the C-arm x-ray imaging system 100.

The rotation of the gantry 102 to which the x-ray source assembly 104 and the x-ray detector array assembly 106 are coupled is controlled by the C-axis controller 138 and the pivot axis controller 140, which respectively control the rotation of the gantry 102 about the C-axis and the pivot axis 116. In response to motion commands from the operator workstation 122, the C-axis controller 138 and the pivot axis controller 140 provide power to motors in the C-arm x-ray imaging system 100 that produce the rotations about the C-axis and the pivot axis 116, respectively. For example, a program executed by the operator workstation 122 generates motion commands to the C-axis controller 138 and pivot axis controller 140 to move the gantry 102, and thereby the x-ray source assembly 104 and x-ray detector array assembly 106, in a prescribed scan path.

The DAS 144 samples data from the one or more x-ray detectors in the x-ray detector array assembly 106 and converts the data to digital signals for subsequent processing. For instance, digitized x-ray data are communicated from the DAS 144 to the data store server 130. The image reconstruction system 132 then retrieves the x-ray data from the data store server 130 and reconstructs an image therefrom. The image reconstruction system 130 may include a commercially available computer processor, or may be a highly parallel computer architecture, such as a system that includes multiple-core processors and massively parallel, high-density computing devices. Optionally, image reconstruction can also be performed on the processor 128 in the operator workstation 122. Reconstructed images can then be communicated back to the data store server 130 for storage or to the operator workstation 122 to be displayed to the operator or clinician.

The C-arm x-ray imaging system 100 may also include one or more networked workstations 148. By way of example, a networked workstation 148 may include a display 150; one or more input devices 152, such as a keyboard and mouse; and a processor 154. The networked workstation 148 may be located within the same facility as the operator workstation 122, or in a different facility, such as a different healthcare institution or clinic.

The networked workstation 148, whether within the same facility or in a different facility as the operator workstation 122, may gain remote access to the data store server 130, the image reconstruction system 132, or both via the communication system 134. Accordingly, multiple networked workstations 148 may have access to the data store server 130, the image reconstruction system 132, or both. In this manner, x-ray data, reconstructed images, or other data may be exchanged between the data store server 130, the image reconstruction system 132, and the networked workstations 148, such that the data or images may be remotely processed by the networked workstation 148. This data may be exchanged in any suitable format, such as in accordance with the transmission control protocol (TCP), the Internet protocol (IP), or other known or suitable protocols.

Similarly, referring to FIGS. 2B and 2C, the imaging system 12 may include a traditional CT system 200, which includes a gantry 202 that forms a bore 204 extending therethrough. In particular, the gantry 202 has an x-ray source 206 mounted thereon that projects a fan-beam, or cone-beam, of x-rays toward a detector array 208 mounted on the opposite side of the bore 204 through the gantry 202 to image the subject 210.

The CT system 200 also includes an operator workstation 212, which typically includes a display 214; one or more input devices 216, such as a keyboard and mouse; and a computer processor 218. The computer processor 218 may include a commercially available programmable machine running a commercially available operating system. The operator workstation 212 provides the operator interface that enables scanning control parameters to be entered into the CT system 200. In general, the operator workstation 212 is in communication with a data store server 220 and an image reconstruction system 222 through a communication system or network 224. By way of example, the operator workstation 212, data store sever 220, and image reconstruction system 222 may be connected via a communication system 224, which may include any suitable network connection, whether wired, wireless, or a combination of both. As an example, the communication system 224 may include both proprietary or dedicated networks, as well as open networks, such as the Internet.

The operator workstation 212 is also in communication with a control system 226 that controls operation of the CT system 200. The control system 226 generally includes an x-ray controller 228, a table controller 230, a gantry controller 231, and a data acquisition system (DAS) 232. The x-ray controller 228 provides power and timing signals to the x-ray module(s) 234 to effectuate delivery of the x-ray beam 236. The table controller 230 controls a table or platform 238 to position the subject 210 with respect to the CT system 200.

The DAS 232 samples data from the detector 208 and converts the data to digital signals for subsequent processing. For instance, digitized x-ray data are communicated from the DAS 232 to the data store server 220. The image reconstruction system 222 then retrieves the x-ray data from the data store server 220 and reconstructs an image therefrom. The image reconstruction system 222 may include a commercially available computer processor, or may be a highly parallel computer architecture, such as a system that includes multiple-core processors and massively parallel, high-density computing devices. Optionally, image reconstruction can also be performed on the processor 218 in the operator workstation 212. Reconstructed images can then be communicated back to the data store server 220 for storage or to the operator workstation 212 to be displayed to the operator or clinician.

The CT system 200 may also include one or more networked workstations 240. By way of example, a networked workstation 240 may include a display 242; one or more input devices 244, such as a keyboard and mouse; and a processor 246. The networked workstation 240 may be located within the same facility as the operator workstation 212, or in a different facility, such as a different healthcare institution or clinic.

The networked workstation 240, whether within the same facility or in a different facility as the operator workstation 212, may gain remote access to the data store server 220 and/or the image reconstruction system 222 via the communication system 224. Accordingly, multiple networked workstations 240 may have access to the data store server 220 and/or image reconstruction system 222. In this manner, x-ray data, reconstructed images, or other data may be exchanged between the data store server 220, the image reconstruction system 222, and the networked workstations 212, such that the data or images may be remotely processed by a networked workstation 240. This data may be exchanged in any suitable format, such as in accordance with the transmission control protocol (TCP), the Internet protocol (IP), or other known or suitable protocols.

To enable accurate low-dose CT imaging, zero counts in the raw output of photon counting detectors (PCDs) must be corrected before the logarithmic transformation. However, currently employed methods for correcting for zeros introduce CT number bias or degrade spatial resolution. The systems and methods described herein provide an explicit derivation of the statistical properties for zero-count corrected PCD-CT imaging data and a correction framework that provides a remedy for zero counts while controlling or compensating for bias, thereby preserving conditional independence, and maintaining spatial resolution.

Using the above-described systems, systems and methods are provided for controlling or managing against errors induced by zero counts in CT data. As will be described, the systems and methods provided herein can address both raw counts (including PCD) and post-logarithm sinogram data. One non-limiting example of correction framework can include (1) replacement of zero-counts in raw CT counts with a non-zero number, which may be a constant, (2) removal of the mean offset induced by the replacement of the zero counts in the raw data, and (3) a data-driven correction step to reduce statistical bias and the bias introduced by the replacement of zero-counts.

Before any zero-count correction, the raw count output, N, of each pixel, which may be a PCD pixel, is given by a Poisson distribution with a probability mass function (PMF) of $$P_N(n) = e^{-\lambda}\frac{\lambda^n}{n!},$$

where $\lambda_i$ is the expected value of N at each detector pixel location, n. The probability of a zero count is therefore related to $\lambda_i$ by $P_N(0)=e^{-\lambda}$.

When N=0, the log-transformation operation, which is necessary to generate the sinogram for reconstruction, cannot be taken over N. The conventional wisdom is to replace zero counts with a non-zero number (which, for example, may be a constant or other positive number), $N_c$, determined empirically or by incorporating values from neighboring pixels (e.g., in low signal correction-based methods). However, the replacement of 0 by $N_c$ changes the statistical distribution of the counts and introduces bias that undermines image accuracy. The PMF of the zero-count corrected counts, Ñ, is given by:

$$P_{\tilde{N}}(n) = \begin{cases} e^{-\lambda \frac{\lambda^n}{n_i!}}, & n = 1, 2, 3, \ldots \\ e^{-\lambda}, & n = N_c \\ 0, & n = 0 \end{cases}, \quad \text{Eqn. (1)}$$

which no longer follow a Poisson form. Consequentially, the $k^{th}$ moment of Ñ becomes:

$$\langle \tilde{N}^k \rangle = 0^k P_{\tilde{N}}(0) + N_c^k P_{\tilde{N}}(N_c) + \sum_{n=1}^{\infty} n^k P_{\tilde{N}}(n) = N_c^k e^{-\lambda} + \langle N^k \rangle. \quad \text{Eqn. (2)}$$

Based on equation (2), there is a statistical bias in Ñ given by:

$$\text{Bias}_{\tilde{N}} = \langle \tilde{N} \rangle - \lambda = N_c e^{-\lambda}. \quad \text{Eqn. (3)}$$

Aside from bias, the impact of the zero-count replacement method on the noise properties of the raw count (PCD) data can be similarly derived from equation 2.

$$\sigma_{\tilde{N}}^2 = \langle \tilde{N}^2 \rangle - \langle \tilde{N} \rangle^2 = \lambda + N_c e^{-\lambda}(N_c - N_c e^{-\lambda} - 2\lambda), \quad \text{Eqn. (4)}$$

where $\sigma_{\tilde{N}}$ is the noise with zero-count corrected counts, Ñ.

Concerning minimizing the variance in the local counts, the optimal selection of $N_c$ can be found from the following:

$$\frac{\partial \sigma_{\tilde{N}}^2}{\partial N_c} = N_c e^{-\lambda}(1 - e^{1\lambda}) + e^{-\lambda}(N_c - N_c e^{-\lambda} - 2\lambda); \quad \text{Eqn. (5)}$$

$$\hat{N}_c = \frac{\lambda}{1 - e^{-\lambda}}, \quad \text{Eqn. (6)}$$

Where $\hat{N}_c$ is a selection of $N_c$ that minimizes the variance of_Ñ.

When considering the bias and noise of the zero-corrected data, the mean squared error (MSE) and the optimal choice of $N_c$ to minimize the MSE can be given by:

$$MSE_{\tilde{N}} = \text{Bias}_{\tilde{N}}^2 + \sigma_{\tilde{N}}^2 = \lambda + N_c e^{-\lambda}(N_c - 2\lambda). \quad \text{Eqn. (7)}$$

$$\hat{N}_c = \lambda e^{\lambda}. \quad \text{Eqn. (8)}$$

When a log transform is applied to the zero count, corrected counts are provided by:

$$\tilde{y} = \ln \langle N_0 \rangle - \ln \tilde{N}. \quad \text{Eqn. (9)}$$

Within this context, the propagation of the bias in Ñ to the sinogram data can be analyzed. A Taylor expansion of equation (9) about λ can be performed to give the corrected counts as:

$$\tilde{y} = \ln\langle N_0 \rangle - \ln\lambda - \frac{1}{\lambda}(\tilde{N} - \lambda) + \frac{1}{2\lambda^2}(\tilde{N} - \lambda)^2 - \frac{1}{3\lambda^3}(\tilde{N} - \lambda)^3 + \ldots . \quad \text{Eqn. (10)}$$

Since the true sinogram is $\ln\langle N_0 \rangle - \ln \lambda$, the statistical bias of the corrected counts, ỹ, is given by:

$$\text{Bias}_{\tilde{y}} = -\frac{1}{\lambda}\langle(\tilde{N} - \lambda)\rangle + \frac{1}{2\lambda^2}\langle(\tilde{N} - \lambda)^2\rangle - \frac{1}{3\lambda^3}\langle(\tilde{N} - \lambda)^3\rangle + \ldots = \sum_{k=1}^{\infty}(-1)^k \frac{1}{k\lambda^k}\langle(\tilde{N} - \lambda)^k\rangle. \quad \text{Eqn. (11)}$$

Based on equations (1) and (11), the bias crated by the corrected counts can be represented by:

$$\text{Bias}_{\tilde{y}} = \sum_{k=1}^{\infty}(-1)^k \frac{1}{k\lambda^k}\left[\langle(\tilde{N} - \lambda)^k\rangle + e^{-\lambda}(N_c - \lambda)^k - e^{-\lambda}(-1)^k \lambda^k\right] \quad \text{Eqn. (12)}$$

Figure 3:
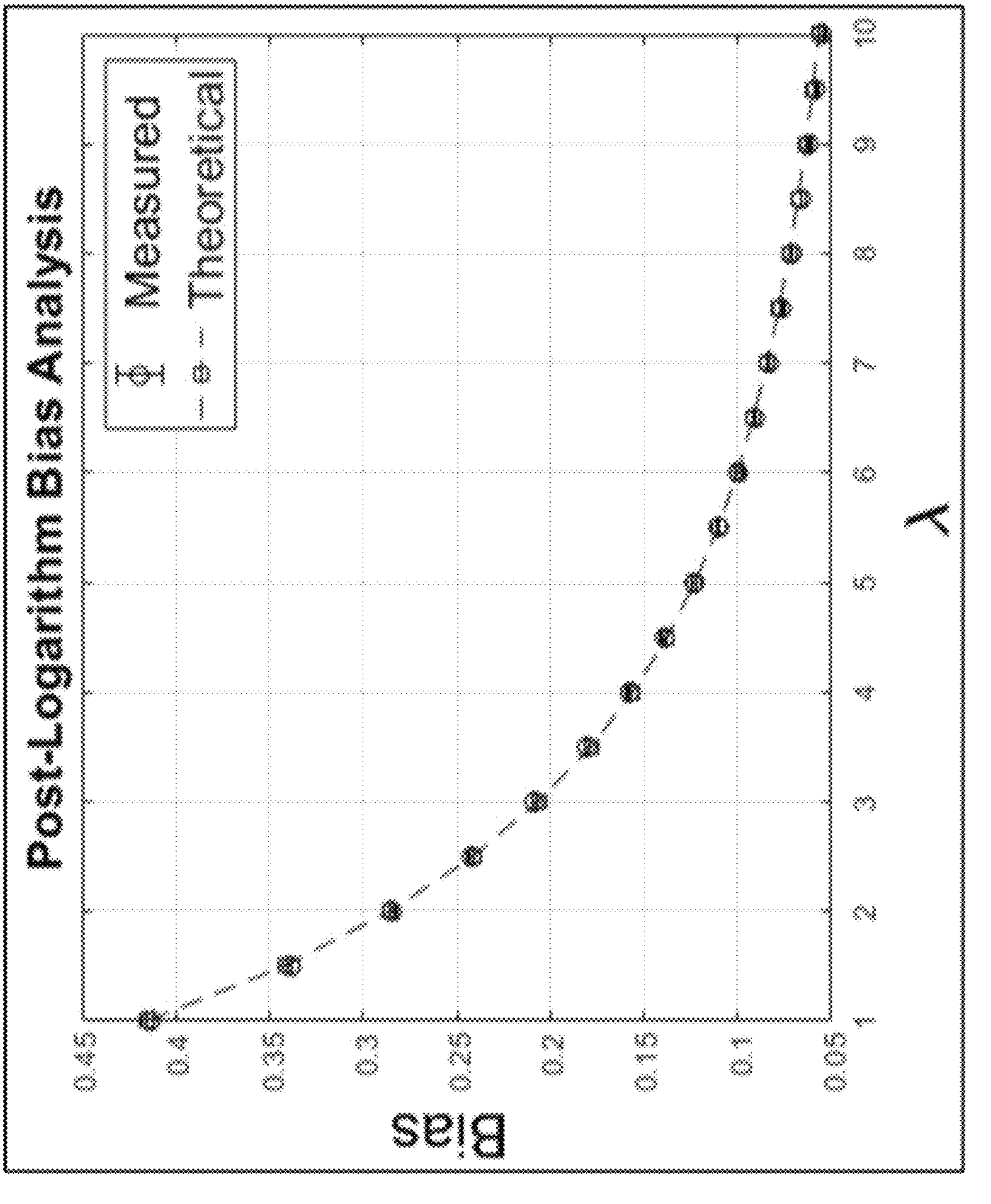
FIG. 3 is a graph showing a comparison of theoretical and measured bias of a sinogram with a zero count-replacement scheme.

Equation (12) shows that there exists a bias in the sinogram jointly determined by λ and $N_c$. FIG. 3 shows biases of the sinogram data when $N_c$ is set to ⅓.

Figure 4:
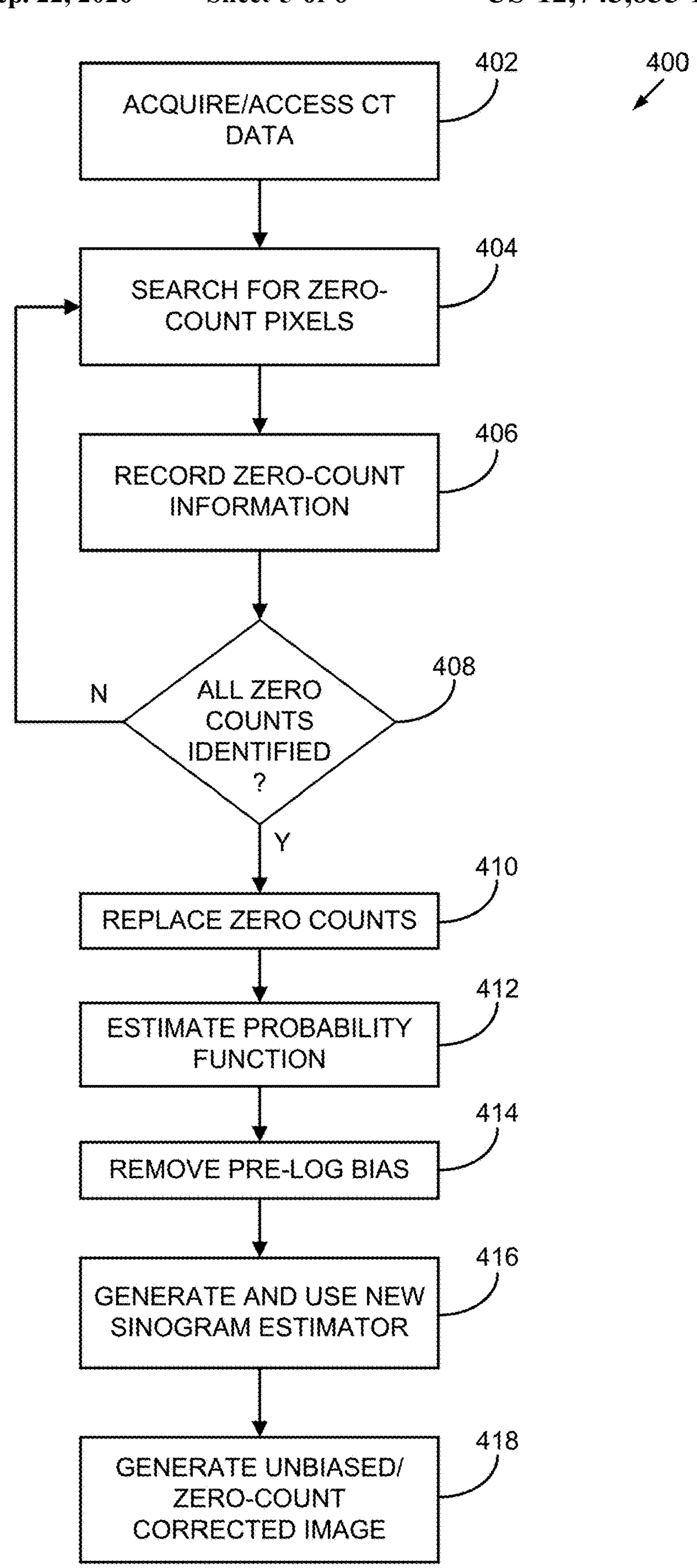
FIG. 4 is a flow chart setting forth some example steps of a process for providing unbiased zero-count correction in accordance with the present disclosure.

With this context and referring to FIG. 4, one non-limiting example of a method 400 for correcting for zero counts without introducing biases is provided. At process block 402, CT data is acquired, such as using the CT system described above, or stored CT data is access, such as described above. The data that is acquired or accessed may include the raw count data. Thus, in the raw counts (N) domain, the processes 400 may include searching for zero-count pixels at process block 404. When one is found, the information about the zero count may be recorded at process block 406, such as, for example, the location and/or number of occurrences. This process may continue until all zero counts are identified at decision block 408. At process block 410, all zero counts can be replaced by $N_c$. At process block 412, for each pixel block (or otherwise defined local region, which can be selected by the user, predefined, or algorithmically defined), $P_N(0)=e^{-\lambda}$ can be estimated, for example, based on the local occurrences of zero counts. In one non-limiting example, PMF relative to the number of zeros in each 10×10 pixel block can be utilized. At process 414, pre-log bias can be removed. For example, because the replacement of all zero counts by $N_c$ at process block 410 introduced a bias of $N_c e^{-\lambda}$, each pixel block can be subtracted by an offset of $N_c P_N(0)$ to remove the pre-log bias, the results of which can be denoted as N". Then, at process block 416, a new sinogram estimator can be constructed with the Laurent expansion of N". That is, to address the biases introduced by the non-linear log operation, a new sinogram estimator can be constructed with the Laurent expansion of N" given by:

$$y^* = \ln\frac{\overline{N}_0}{N''} + \sum_{k=1}^{K}\frac{C_k}{\tilde{N}^k}, \quad \text{Eqn. (13)}$$

where coefficients $C_k$ can be determined from calibration data with known ln $$\frac{\overline{N}_0}{\lambda}.$$

In one non-limiting example, the total number of coefficients found to be sufficient for the Laurent expansion bias model was K=4, and the optimal values were found to be $C_1$=0.502 [95% CI: 0.499, 0.506], $C_2$=−0.086 [ 95% CI: −0.099, −0.072], $C_3$=−0.022 [95% CI: −0.029, −0.015], and $C_4$=0.005 [95% CI: 0.004, 0.006]. Thus, the process described above with respect to FIG. 4 and its implementation within the systems of FIGS. 1-2C provide a correction framework that corrects for zero counts while controlling or compensating for bias, thereby preserving conditional independence, and maintaining spatial resolution.

EXAMPLE

Experimental PCD-CT data were acquired from a benchtop system The system had a CdTe-based PCD with 51 cm axial coverage and 0.1 mm pixels. An angio tube (G1952 with B-180H housing, Varex) was operated at 120 kV. The source-to-iso and source-to-detector distances were 57 cm and 103 cm, respectively. Experiments were performed at a high dose level of $CTDI_{vol}$ (16 cm phantom)=48 mGy (320 mAs) and a low dose level of 3 mGy (20 mAs). Each scan acquired one thousand two hundred projection views and was uniformly distributed over 360 degrees. Image reconstruction was performed using standard Filtered backprojection (FBP).

For a quantitative analysis of the CT number bias using the above-described correction framework, the CTP404 module of a Catphan 600 phantom, an anthropomorphic head phantom (ACS CT Head, Kyoto Kagaku), and a dual-energy phantom with 6 Gammex iodine and calcium inserts were scanned. Reference gold standard images were generated from ensemble averaging of 26 repeated acquisitions at the 48 mGy dose level. For a dual energy experiment, the PCD-CT was operated with the low and high energy thresholds at 15 keV and 63 keV respectively. Following the application of the above-described correction process, low- and high-energy PCD-CT images were reconstructed and an image-domain, two-material decomposition was performed to generate post-correction water and iodine basis images.

Figure 5:
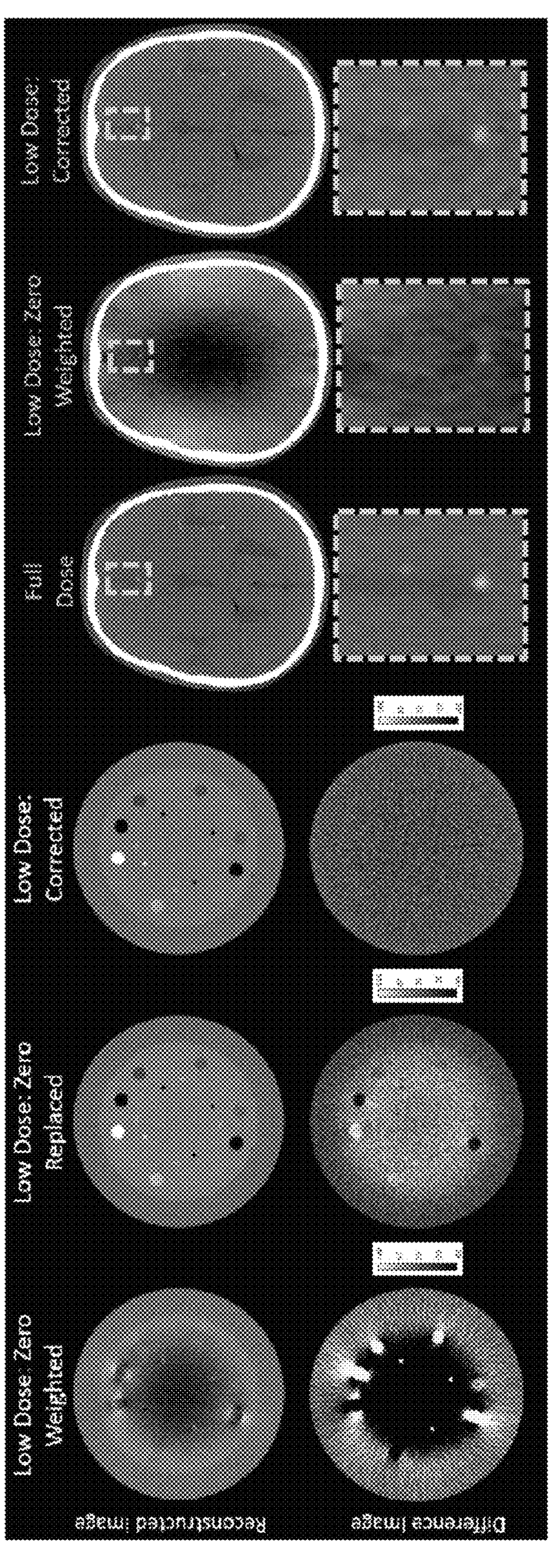
FIG. 5 is a set of correlated images including low-dose PCD-CT images of a Catphan phantom and images of a head phantom, as well as difference images relative to a high-dose gold standard.

As shown in FIG. 5, conventional zero-count corrections resulted in significant degradation of the image quality and CT number biases. For example, the appearance of "ghost inserts" can be seen in the difference image. Using the systems and method described herein, the manifestation of "ghost inserts" are not present, indicating that the bias has been removed because the "ghost inserts" are not present when the corrected imagines are reconstructed. This is further demonstrated by the quantitative results presented in Table 1.

TABLE 1

Comparison of CT number biases for different zero-count methods.

| Material Insert | Bias: Zero Weighted [HU] | Bias: Zero Replaced [HU] | Bias: Corrected [HU] |
|---|---|---|---|
| Delrin | 113 ± 5 | 81 ± 1 | 1 ± 1 |
| Teflon | −47 ± 11 | 120 ± 1 | 7 ± 1 |
| Air | −30 ± 10 | −62 ± 1 | 0 ± 1 |
| PMP | 98 ± 1 | 31 ± 1 | −1 ± 1 |
| LDPE | 127 ± 1 | 40 ± 1 | −1 ± 1 |
| PS | 103 ± 1 | 46 ± 1 | −1 ± 1 |
| Acrylic | 111 ± 2 | 59 ± 1 | 0 ± 1 |
| Center | −389 ± 5 | 48 ± 1 | 3 ± 1 |

Figure 6:
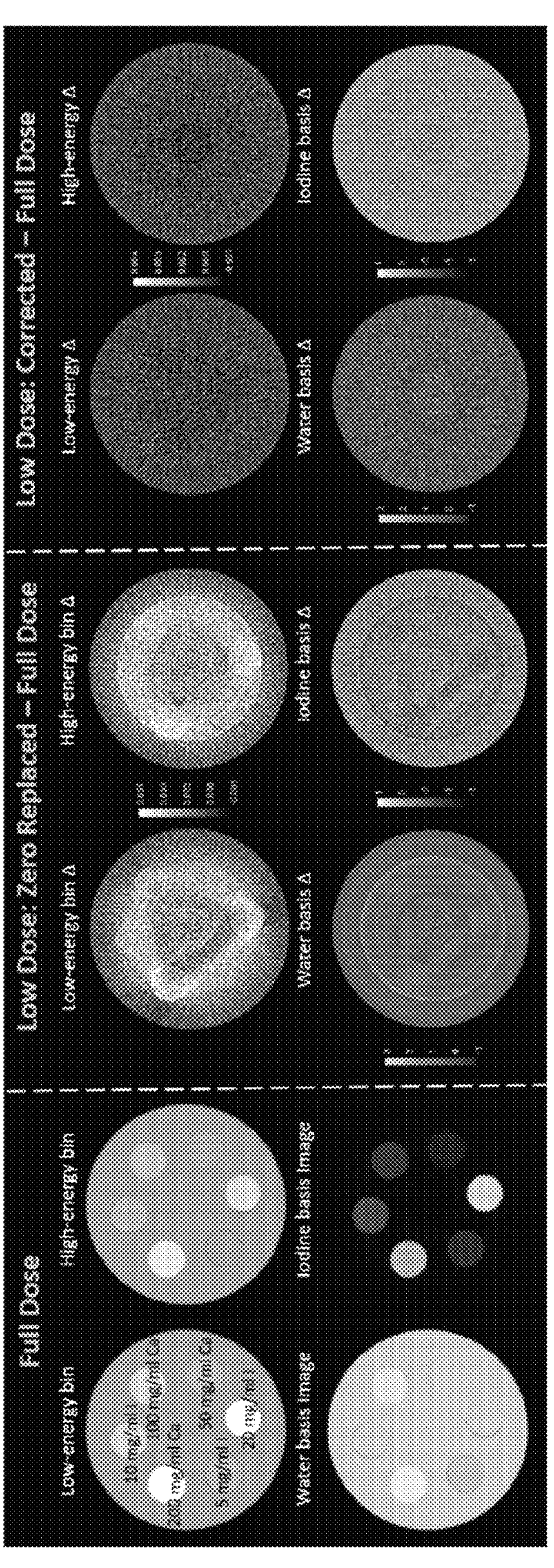
FIG. 6 is a set of correlated images including high- and low-energy bin results of Gammex inserts for the full dose images, as well as water- and iodine-basis results.
Figure 7:
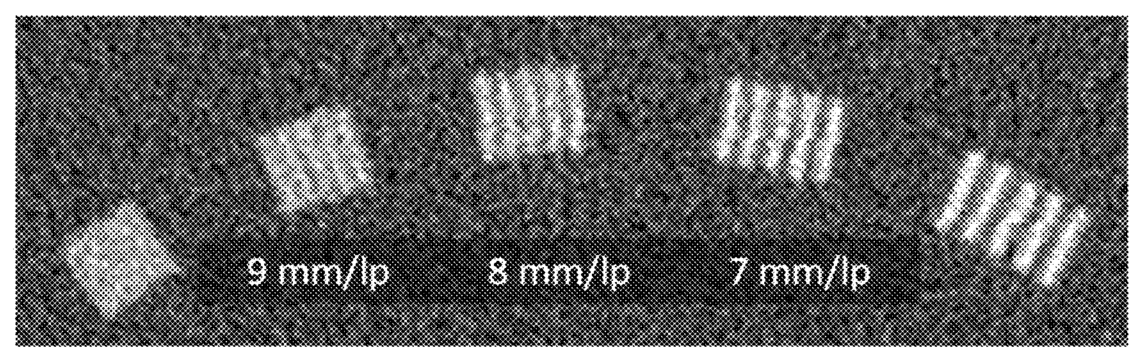
FIG. 7 is a set of correlated images of line pair patterns for corrected and zero-weighted CT data.
Figure 7:
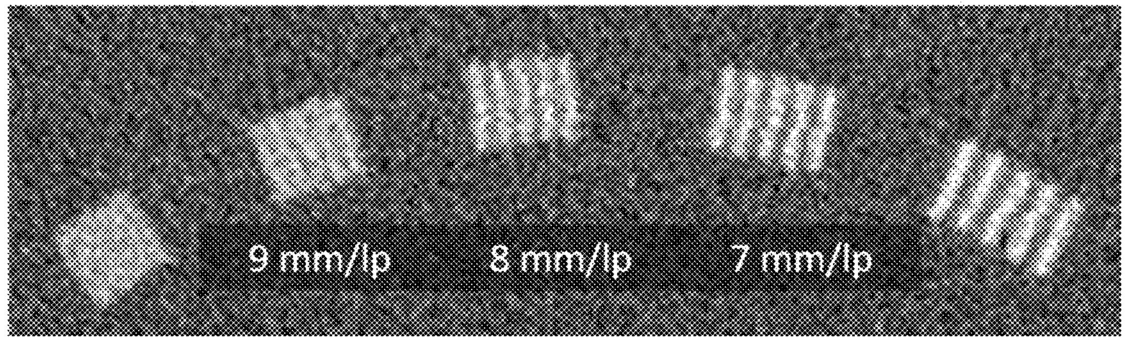

The dual-energy PCD-CT energy bin and material basis images presented in FIG. 6 similarly validate the efficacy of systems and methods presented herein when photon counts are split between multiple energy bins. FIG. 5 also shows images of the anthropomorphic head phantom. The low-dose corrected image demonstrates preserved anatomical features compared to the full dose reference standard. For example, the intraparenchymal hemorrhage models can be distinguished as illustrated by the zoomed-in portion of the figure. Zero weighting results in a significant loss of anatomical features and the obfuscation of many intraparenchymal hemorrhage models, highlighting the importance of appropriate zero-count corrections. Finally, images of the line pair patterns shown in FIG. 7 confirm that the systems and methods provided herein do not degrade the spatial resolution of PCD-CT images. This is the result of the systems and methods provided herein operating on individual pixels without additional spatial filtration.

The systems and methods provided herein may be combine with other techniques for overcoming limitations with PCD systems, as they are applied to clinical settings. For example, U.S. Ser. No. 17/512,236, filed Oct. 27, 2021, describes systems and methods for controlling errors in computed tomography data with raw detector count data, and is incorporated herein by reference in its entirety. Also, U.S. Ser. No. 17/971,617, filed Oct. 23, 2022, describes systems and methods for controlling scatter in computed tomography data, and is incorporated herein by reference in its entirety. Further, U.S. Ser. No. 17/987,917, filed Nov. 16, 2022, describes systems and methods for controlling errors in CT number without requiring raw detector count data, and is incorporated herein by reference in its entirety.

Addressing the issue of zero-counts is paramount for achieving high-quality and accurate low-dose PCD-CT imaging, as is desired for clinical applications. The system and methods provided herein provide a zero-count correction framework that has been demonstrated to 1) reduce the bias introduced by the replacement of zeros in the pre-logarithm PCD counts, 2) mitigate the impact of the statistical bias introduced by the logarithmic transform in the post-logarithm PCD data, and 3) preserve the spatial resolution of the final reconstructed images. The utility and generalizability of the systems and methods provided herein were demonstrated through a series of phantom imaging studies. In addition to preserving the spatial resolution, another advantage of the systems and methods provided herein is the high computational efficiency, because only a single pass is needed to correct the zero counts. That is, the present systems and methods do not require iterative processing to correct for zero counts.

As used herein, the phrase "at least one of A, B, and C" means at least one of A, at least one of B, and/or at least one of C, or any one of A, B, or C or combination of A, B, or C. A, B, and C are elements of a list, and A, B, and C may be anything contained in the Specification.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for creating computed tomography (CT) images comprising:

acquiring or accessing CT data of a subject;

identifying zero counts in the CT data;

replacing the zero counts in the CT data with at least one non-zero number to create zero-count free CT data;

estimating a probability function of the zero-count free CT data;

removing bias in the zero-count free CT data using the probability function; and reconstructing the zero-count free CT data after removal of the bias to create a corrected image of the subject with preserved conditional independence and spatial resolution.

2. The method of claim 1, wherein estimating the probability function is performed for each of a plurality of local pixel regions.

3. The method of claim 2, wherein estimating the probability function includes calculating a probability mass function relative to a number of zero counts replaced in a given local pixel region.

4. The method of claim 1, wherein the bias is a function of an expected raw count output at each pixel location in the CT data ($\lambda$) and the non-zero number ($N_c$).

5. The method of claim 4, wherein the bias is determined using $N_c e^{-\lambda}$.

6. The method of claim 5, wherein removing the bias includes subtracting an offset of $N_c P_N(0)$ from each pixel, where $P_N(0)=e^{-\lambda}$ is an estimated probability of a zero count at a pixel.

7. The method of claim 1, wherein removing bias in the zero-count free CT data further comprises constructing a new sinogram estimator that addresses biases introduced by a non-linear log operation and using the new sinogram estimator to generate a sinogram for reconstructing the zero-count free CT data.

8. A method for creating computed tomography (CT) images comprising:

acquiring or accessing CT data of a subject;

identifying zero counts in the CT data;

replacing the zero counts in the CT data with at least one non-zero number to create zero-count free CT data;

reducing a pre-log bias in the zero-count free CT data introduced by replacing of the zero counts with the at least one non-zero number;

generating a sinogram estimator;

reducing a post-log bias in the zero-count free CT data using the sinogram estimator; and reconstructing the zero-count free CT data after reducing the pre-log bias and the post-log bias to create an image of the subject.

9. The method of claim 8, wherein reducing the pre-log bias includes removing the mean offset in the zero-count free CT.

10. The method of claim 8, wherein reducing the pre-log bias includes estimating a probability mass function relative to a number of zero counts replaced in a given local pixel region.

11. The method of claim 8, wherein the reducing the pre-log bias includes determining the pre-log bias using $N_c e^{-\lambda}$, wherein $\lambda$ is an expected raw count output at each pixel location in the CT data and $N_c$ is the at least one non-zero number.

12. The method of claim 11, wherein reducing the pre-log bias includes subtracting an offset of $N_c P_N(0)$ from each pixel, where $P_N(0)=e^{-\lambda}$ is an estimated probability of a zero count at a pixel.

13. The method of claim 8, reducing post-log bias includes constructing the sinogram estimator to address biases introduced by a non-linear log operation and using the sinogram estimator to generate a sinogram for reconstructing the zero-count free CT data.

* * * * *